United States Patent [19]

Menju et al.

[11] 4,231,258

[45] Nov. 4, 1980

[54] METHOD AND APPARATUS FOR DETECTING FOREIGN MATTERS IN GAS SEALED ELECTRIC APPARATUS

[75] Inventors: Shinichi Menju, Atsugi; Kunio Takahashi, Yokohama; Eiichi Haginomori, Tokyo; Yoichi Murakami, Yokohama; Eiichi Zaima, Tokyo, all of Japan

[73] Assignees: Tokyo Shibaura Denki Kabushiki Kaisha; Tokyo Denryoku Kabushiki Kaisha, both of Tokyo, Japan

[21] Appl. No.: 571

[22] Filed: Jan. 2, 1979

[30] Foreign Application Priority Data

Jan. 19, 1978 [JP] Japan .................................. 53-3711
Jan. 19, 1978 [JP] Japan .................................. 53-3712

[51] Int. Cl.³ .......................................... G01N 29/04
[52] U.S. Cl. .................................................... 73/572
[58] Field of Search ...................... 73/572, 587; 324/54

[56] References Cited

U.S. PATENT DOCUMENTS

| | | | |
|---|---|---|---|
| 3,505,597 | 4/1970 | Cronin et al. | 324/72 |
| 3,612,992 | 10/1971 | Cronin | 324/52 |
| 3,622,872 | 11/1971 | Boaz | 324/52 |
| 4,158,169 | 6/1979 | Harrold et al. | 324/54 |

*Primary Examiner*—Anthony V. Ciarlante
*Attorney, Agent, or Firm*—Stevens, Davis, Miller & Mosher

[57] ABSTRACT

In a method for detecting foreign matters present in gas sealed electrical apparatus including a tank at the ground potential and containing an insulating gas and a high voltage live part disposed in the tank, a voltage is applied to the high voltage live part causing generation of ultrasonic waves and the ultrasonic waves propagated through the tank is sensed by a sensing element mounted on the tank.

2 Claims, 11 Drawing Figures

F I G. 5A
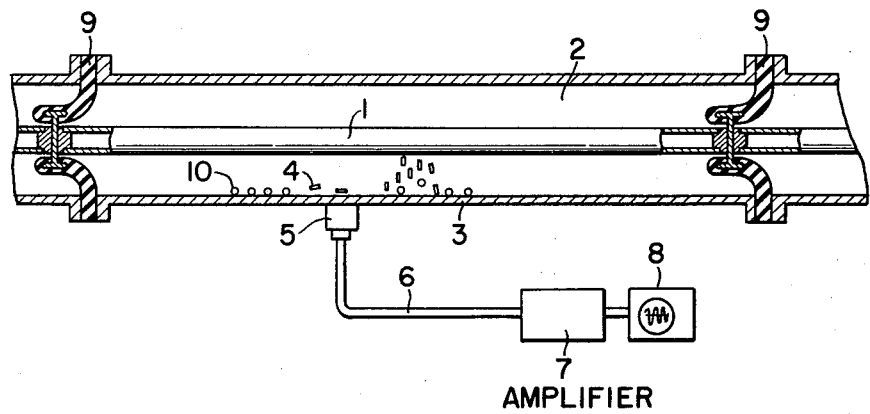
F I G. 5B
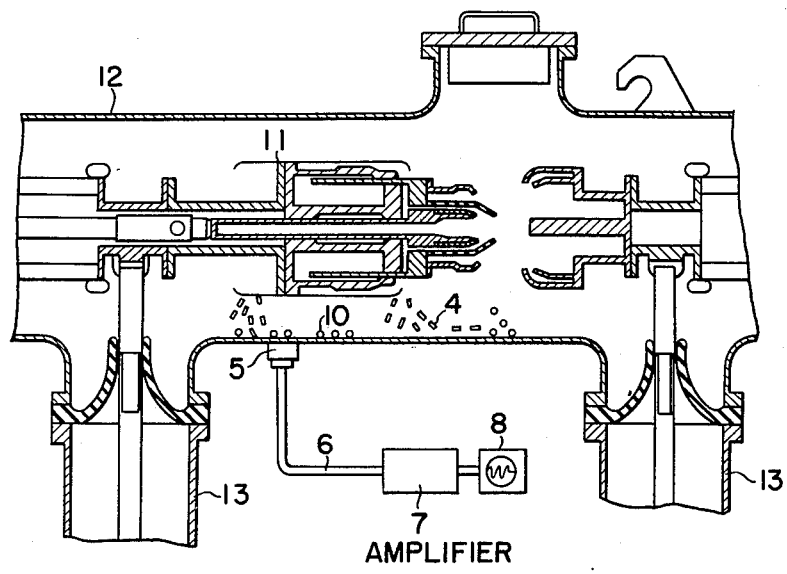

METHOD AND APPARATUS FOR DETECTING FOREIGN MATTERS IN GAS SEALED ELECTRIC APPARATUS

BACKGROUND OF THE INVENTION

The present invention relates to a method and apparatus for detecting foreign matters in a gas sealed electrical apparatus.

One of the problems associated with sealed type gas insulated electrical apparatus is the presence of foreign matters, such as metallic particles, in the electric apparatus. Such foreign matters may be produced by friction or sliding at the contacting surfaces of metallic parts during assembly in the factory or in the site at which the electrical apparatus is installed. The foreign matters may also be introduced while the interior of the electrical apparatus is exposed to the atmosphere before the electrical apparatus is sealed. The presence of the foreign matters in a circuit breaker, a disconnecting switch or a grounding switch is also attributable to local fusion of the movable and stationary contacts due to frictional heat or arcing. If a high voltage is applied to the electrical apparatus with metallic foreign matters contained therein, insulation breakdown occurs at a voltage several times lower than the insulating strength of the apparatus free from any metallic foreign matters or at even lower voltages. With large sized electrical apparatus, it is impossible to accuratily locate the portion of the apparatus where the initial breakdown has occurred. In order to locate the portion of initial breakdown, the whole electrical apparatus must be disassembled, which is time-consuming and laborious.

The insulation breakdown thus caused of course leads to disturbance in the power transmission system. Moreover, the parts damaged by the breakdown need to be disassembled and repaired.

In general, metallic particles contained in sealed type gas insulated electrical apparatus move under electric field and gravity at the bottom of the grounded tank portion in a manner described below. In FIG. 1, an electrical apparatus is shown in a simplified form for brevity of description. The electrical apparatus comprises a cylindrical grounded casing or tank 3 constituting an electrode and a central conductor 1 constituting a second electrode. The space between the casing 3 and the central conductor 1 is filled with an insulating gas 2. Present at the bottom of the tank 3 is a needle-shaped metallic particle 4. When no voltage is applied to the central conductor 1, the metallic particle 4 is at rest, as shown at (a) in FIG. 1. As a voltage is applied to the central conductor 1, electrostatic force is exerted on the metallic particle. As the voltage is increased the electrostatic force is increased. As the electrostatic force overcomes the force of gravity, the metallic particle is made to stand as shown at (b) and (c) in FIG. 1. When the voltage is increased further, the metallic particle moves up, and floats in the gas and reaches the central conductor 1 as shown at (c), (d), (e) in FIG. 1. When the electrostatic force becomes smaller than the force of gravity, or when the direction of the electrostatic force is reversed, the metallic particle 4 falls down as shown at (e), (f) and (g) in FIG. 1 and, upon collision with the bottom of the grounded tank 3, generates elastic waves, essentially consisting of ultrasonic waves. With a needle-shaped metallic particle, the electrostatic force is proportional to the square of the length of the particle, whereas the force of gravity is directly proportional to the length of the particle, so that the longer the particle is, the more active the movement of the particle is, and the greater the generated elastic waves are. With a globular metallic particle, the electrostatic force is proportional to the square of the radius of the particle, whereas the force of gravity is proportional to the cube of the radius of the particle, so that larger the radius of the particle is, the less active the movement of the particle is. In any case, the metallic part 4 actively moves about in the space between the central conductor 1 and the grounded tank 3, and during the up-and-down movement of the metallic particle insulation breakdown occurs at a voltage much lower than the breakdown voltage in the absense of the metallic particle.

The elastic waves, including the ultrasonic waves, are also caused by corona discharge which occurs at a lower voltage than if no metallic particles are present.

FIG. 2 shows an example of electrical apparatus which may be affected by the presence of metallic particles. A central conductor 1 is supported by a grounded casing 3 through insulating spacers 9 which contain joints 9a for interconnecting adjacent sections of the conductor 1. If globular metallic particles 10 or needle-shaped metallic particles 4 are present, insulation breakdown occurs at a low voltage.

Similar problem also occurs in gas filled circuit breakers.

SUMMARY OF THE INVENTION

An object of the invention is to provide a method and apparatus for detecting metallic particles present in gas sealed electrical apparatus.

Another object of the invention is to enable location of metallic particles present in gas sealed electrical apparatus.

According to one aspect of the present invention, there is provided a method for detecting foreign matters present in gas sealed electrical apparatus including a tank at the ground potential and containing an insulating gas and a high voltage live part disposed in the tank, characterized by the steps of applying a voltage to the high voltage live part for causing generation of ultrasonic waves and propagation thereof through the tank, sensing the ultrasonic waves propagated through the tank, and discriminating between the magnitudes of the sensed ultrasonic waves to determine the shape of the foreign matters.

According to another aspect of this invention there is provided apparatus for detecting foreign matters present in gas sealed electrical apparatus including a tank at the ground potential containing an insulating gas and a high voltage live part disposed in the tank, characterized in that said detecting apparatus comprises sensing means located on said tank for sensing ultrasonic waves generated by foreign matters present in said tank and propagating through the tank, and indicating means responsive to the output of said sensing means for indicating the presence of said foreign matters.

BRIEF DESCRIPTION OF THE DRAWINGS

In the accompanying drawings:

FIG. 5A shows the detection apparatus of FIG. 4 attached to a gas filled bus bar;

FIG. 5B shows the detection apparatus of FIG. 4 attached to a gas filled circuit breaker;

DESCRIPTION OF THE PREFERRED EMBODIMENTS

Figure 1:
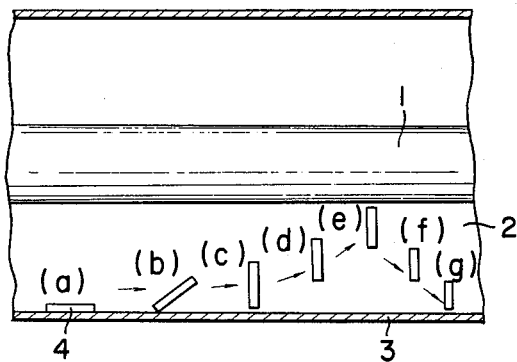
FIG. 1 shows a longitudinal section of an electrical apparatus schematically illustrating how a needle shaped metallic particle moves in the electrical apparatus under electric field and gravity.
Figure 2:
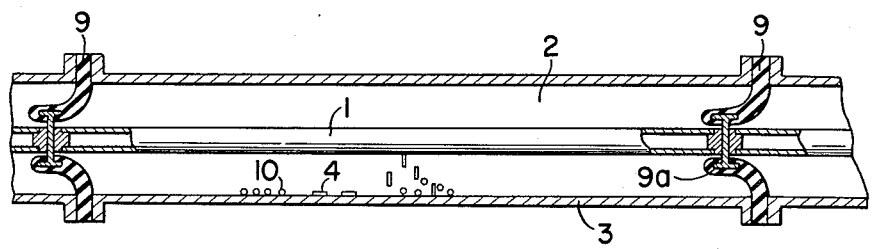
FIG. 2 shows a longitudinal section of a gas filled bus bar with metallic particles contained therein.
Figure 3:
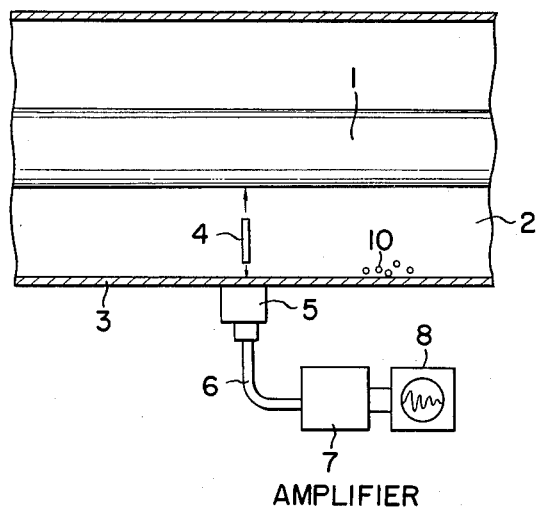
FIG. 3 shows an embodiment of a detection apparatus according to the invention, attached to an electrical apparatus.

Referring now more particularly to FIG. 3, there is shown detection apparatus embodying the invention. A high voltage central conductor 1 is built in a grounded casing or tank 3, which contains an insulating gas 2. A needle-shaped metallic particle 4 and globular metallic particles 10 are present in the casing 3. When a voltage is applied to the central conductor 1, metallic particles 4 and 10 move up and down, and produce elastic waves, essentially consisting of ultrasonic waves, upon collision with the grounded casing 3. The elastic waves are also produced by corona discharge which occurs at a lower voltage than if no metallic particles are present. An ultrasonic wave sensing element 5, such as a piezoelectric element, is mounted to the exterior of the grounded casing 3 to sense the ultrasonic waves propagated through the casing 3, and converts the ultrasonic waves into an electrical signal. A cable 6 connects the sensing element 5 to an amplifier 7, whose output is fed to an indicating device 8, such as a synchroscope or a digital memory device, to enable observation. Thus presence of the metallic particles in the grounded casing 3 can be detected by the indication of the indicating device 8.

Figure 4:
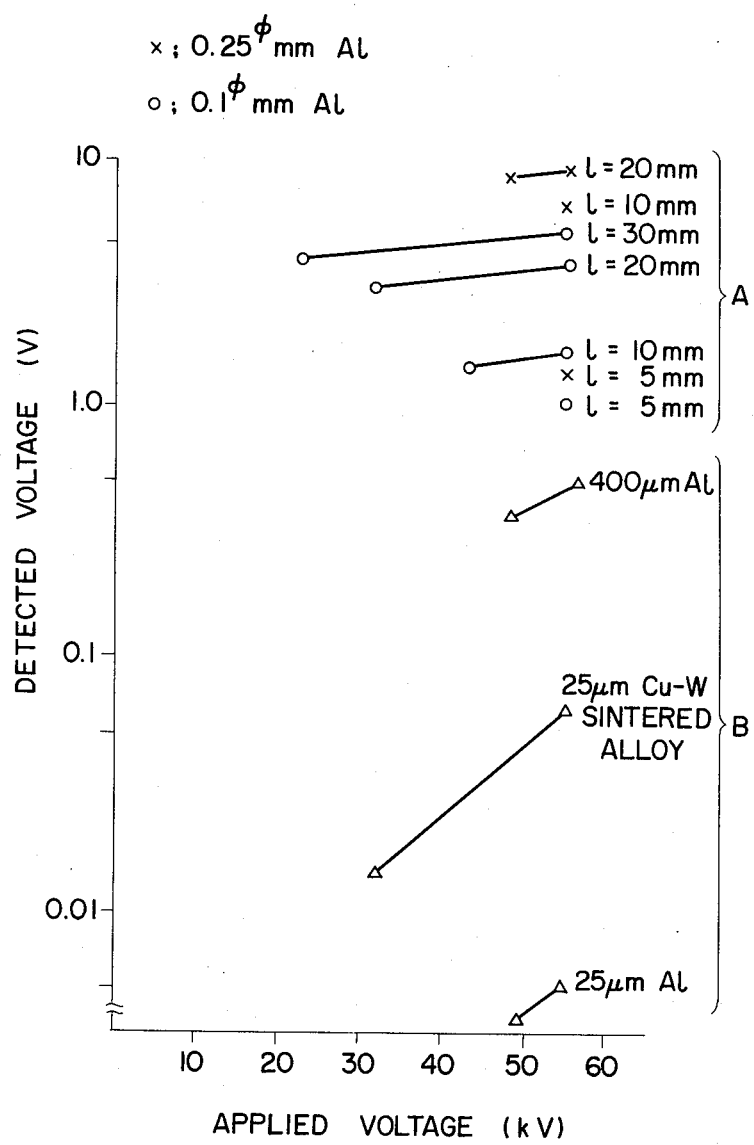
FIG. 4 is a graph showing the magnitudes of the output of the sensing element in relation to the applied voltage.

FIG. 4 shows the output produced by the ultrasonic sensing device 5. The plots grouped by a bracket A are those obtained when the needle shaped metallic particles are present. The plots grouped by a bracket B are those obtained when the globular metallic particles are present. With the presence of the needle shaped metallic particles, the output voltages are at about or over a level of 1 V. Longer metallic particles are found to result in greater output voltages. With the presence of the globular metallic particles, the detected voltage are at about or below a level of 0.5 V. It is therefore possible to discriminate between the magnitudes of the waves to determine whether the metallic particles present are needle shaped ones or globular ones. In other words, one may judge that the particles present are needle shaped if the output of the sensing device is above a certain level (0.75 V, for example), and that the particles present are globular if the output of the sensing device is below the level.

FIGS. 5A and 5B respectively show ultrasonic sensing devices 5 attached to gas filled bus bar and circuit breaker. In the circuit breaker shown in FIG. 5B, relatively movable contacts 11 are contained in a gas filled casing 12 and these contacts are connected to gas filled bus bars 13. In each case, the indicating device 8 permits observation of the ultrasonic waves due to the presence of the metallic particles 4 and 10 in a grounded casing 3 and 12. By the use of the detecting apparatus, dielectric breakdown can be prevented.

Figure 6:
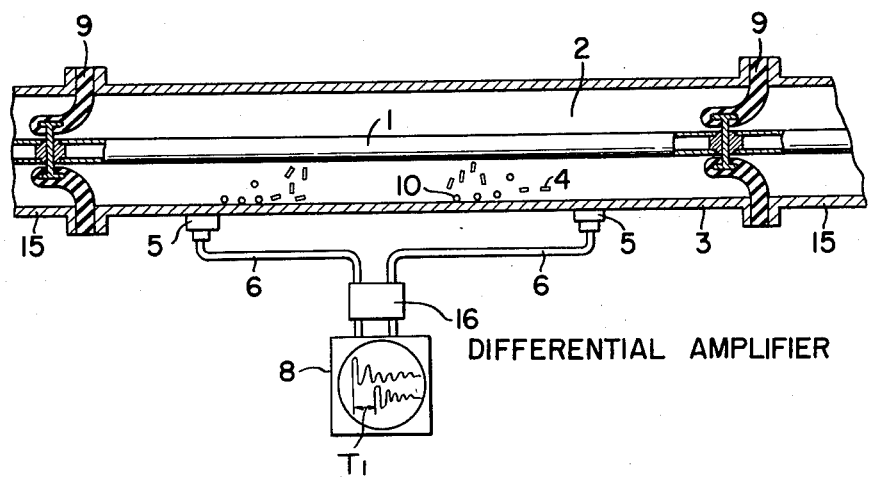
FIG. 6 shows another embodiment of the invention with two sensing elements at different positions.

In FIG. 6, at least two sensing elements 5 are mounted at different positions on the same grounded casing 3 (or to the different casings 3, 15), and a single indicating device 8 is connected to both sensing elements for simultaneously indicating two input voltages. The time lag $T_1$ of one voltage wave behind the other is measured, and, used together with the propagation velocity of the ultrasonic wave through the grounded casings 3 and 15 for calculation necessary to locate the metallic particles. If a differential amplifier 16 is employed, external mechanical low-frequency noises transmitted to the grounded casings 3 and 15 and sensed by the sensing elements 5 can be removed. Thus, accuracy of the measurement is improved.

Figure 7:
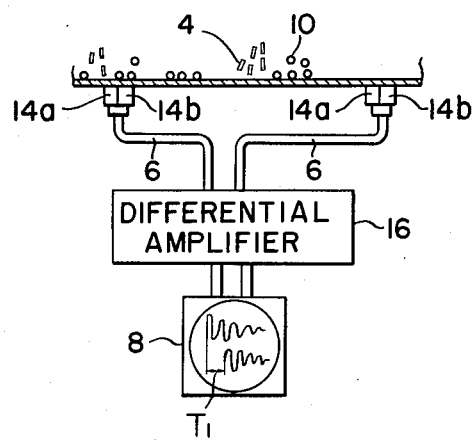
FIG. 7 shows a further embodiment of the invention with two sensing elements of different polarities mounted at the same positions.

As shown in FIG. 7, differential sensing elements $14_a$ and $14_b$ of different polarities are mounted at the same positions and adapted to perform an additional differential operation. By the additional differential operation, the sensitivity of the measurement is improved.

The detecting apparatus illustrated in FIG. 5A, 5B, 6, 7 and 8 are relatively bulky and require an AC power source. These are disadvantageous in certain applications. Also, to conduct detection of metallic particles in an electrical apparatus placed at a high spot, a special support may be required.

Figure 8:
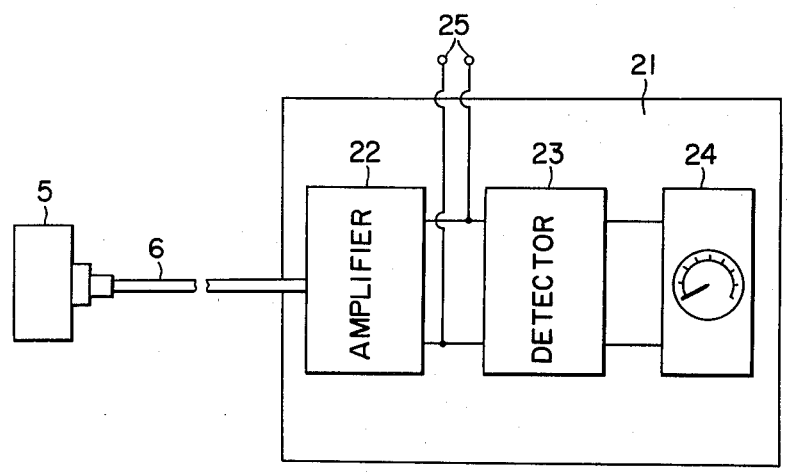
FIG. 8 shows a further embodiment of the invention with a simplified measurement device, and FIGS. 9 and 10 respectively show different variations of the simplified measurement device.

FIG. 8 shows another embodiment of the invention. The output of an ultrasonic sensing element 5 is supplied via a cable 6 to an amplifier 22 and is amplified there to a sufficient level. The output of the amplifier 22 is detected by a detector 23 to be transformed to a waveform suitable for driving a direct-reading indicator such as a pointer type meter 24. The meter 24 may be a crest meter or a mean value meter. The amplifier 22, the detector 23 and the meter 24 form a simplified measurement device 21 and are all energized by a portable type source such as a battery (such as dry cells or cadmium cells) and hence do not require an AC power source. If the reading on the meter 10 is greater than a specific value, presence of metallic particles is assumed.

Terminals 25 are provided at the output of the amplifier 7 to permit connection of a synchroscope, by which the waveform of the voltage can be observed so that it can be determined whether the metallic particles present are needle shaped or globular and what the size of the metallic particles is.

Figure 9:
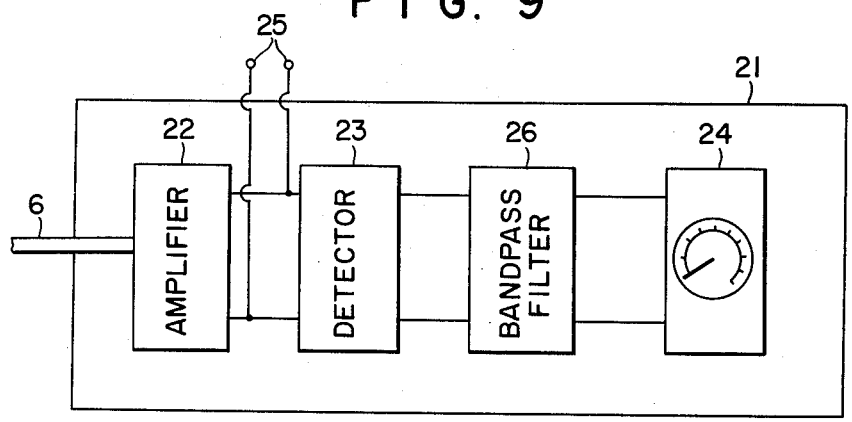

As shown in FIG. 9, a bandpass filter 26 may be inserted between the detector 23 and the meter 24 so that only the detected voltage of a preselected frequency is fed to the meter 10. Such insertion of the bandpass filter 26 is useful for suppressing noises, to supply the meter 24 with a signal indicative of the ultrasonic waves having noises removed.

Figure 10:
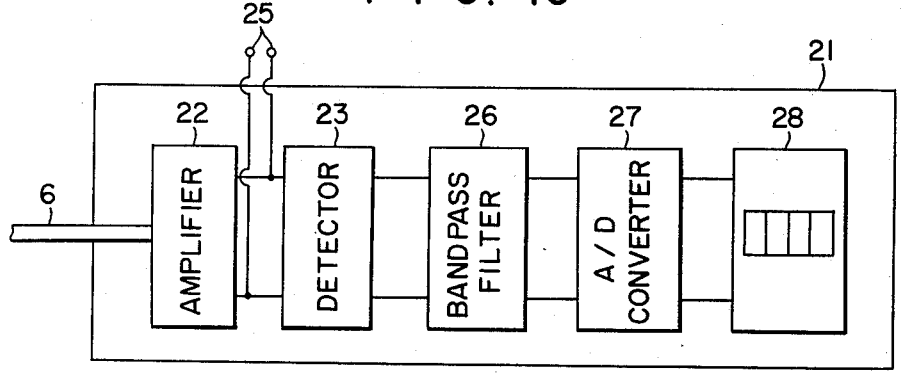

FIG. 10 shows a further embodiment of the invention. The pointer type meter 24 of FIG. 10 is replaced by an analog to digital converter 27 and a digital indicator 28.

What is claimed is:

1. In a method for detecting for the presence of foreign matter in a gas sealed electrical apparatus including a tank at ground potential and containing an insulating gas and having a high voltage live element disposed in the tank, the improvement which comprises:

applying a voltage to the high voltage live element for causing generation of ultrasonic waves by collision of foreign matter with the tank, said waves being propagated through the tank;

sensing the ultrasonic waves produced by said collision which are propagated through the tank; and, indicating the magnitude of the sensed ultrasonic waves to enable determination of the shape of the foreign matter.

2. A method as set forth in claim 1, wherein the step of sensing comprises sensing the ultrasonic waves at a plurality of spaced positions on the tank, said method further comprising detecting and indicating the time difference between the sensings of the ultrasonic waves at said positions and calculating the location of the foreign matter from said detected time differences.

* * * * *